United States Patent
Ripley

(10) Patent No.: US 7,609,068 B2
(45) Date of Patent: Oct. 27, 2009

(54) SYSTEM AND METHOD FOR PARTICULATE SENSOR DIAGNOSTIC

(75) Inventor: Eugene V. Ripley, Russiaville, IN (US)

(73) Assignee: Delphi Technologies, Inc., Troy, MI (US)

( * ) Notice: Subject to any disclaimer, the term of this patent is extended or adjusted under 35 U.S.C. 154(b) by 194 days.

(21) Appl. No.: 11/867,404

(22) Filed: Oct. 4, 2007

(65) Prior Publication Data

US 2009/0090622 A1    Apr. 9, 2009

(51) Int. Cl.
G01R 31/28 (2006.01)
(52) U.S. Cl. .................. 324/512; 324/500; 324/522; 324/523; 324/527; 324/537
(58) Field of Classification Search .............. 324/500, 324/512, 519, 522, 525, 527, 537, 538
See application file for complete search history.

(56) References Cited

U.S. PATENT DOCUMENTS

| | | | | |
|---|---|---|---|---|
| 5,898,107 | A * | 4/1999 | Schenk | 73/114.71 |
| 6,164,125 | A * | 12/2000 | Kawase et al. | 73/114.73 |
| 6,634,210 | B1 | 10/2003 | Bosch et al. | |
| 6,996,499 | B2 * | 2/2006 | Kurokawa et al. | 702/185 |
| 7,075,307 | B1 * | 7/2006 | Williamson | 324/519 |
| 7,152,474 | B2 * | 12/2006 | Deb et al. | 73/514.32 |
| 7,514,937 | B2 * | 4/2009 | Mirov et al. | 324/538 |
| 2004/0164755 | A1 * | 8/2004 | Yamaoka et al. | 324/754 |
| 2006/0123289 | A1 * | 6/2006 | Williams | 714/724 |
| 2008/0019063 | A1 * | 1/2008 | Muller et al. | 361/42 |
| 2008/0020627 | A1 * | 1/2008 | Sexton et al. | 439/404 |
| 2008/0231286 | A1 * | 9/2008 | Tsunekazu et al. | 324/509 |

FOREIGN PATENT DOCUMENTS

JP         11006812 A  *  1/1999

* cited by examiner

Primary Examiner—David A. Rogers
(74) Attorney, Agent, or Firm—Paul L. Marshall

(57) ABSTRACT

A particulate (soot) sensor system has a diagnostic feature for verifying the integrity of the wiring leads. The sensor system includes a sensor and processing circuitry. The sensor has a substrate, first and second sensing electrodes on the substrate and a heater electrode. The heater electrode is electrically isolated from the first and second sensing electrodes, although there is a parasitic capacitance between them. The processing circuitry includes a heater driver, a measurement circuit connected to the sensing electrodes by wire leads, and a detector. The heater driver, in addition to energizing the heater, produces a stimulus signal that is applied to the heating electrode, which is then coupled via the parasitic capacitance to the sensing electrodes. The detector is coupled to the wiring leads and is configured to detect the stimulus signal when there is electrical conductivity over the leads to the sensing electrodes.

13 Claims, 3 Drawing Sheets

SYSTEM AND METHOD FOR PARTICULATE SENSOR DIAGNOSTIC

TECHNICAL FIELD

This invention relates generally to particulate sensor systems, and more particularly to a system and method for a particulate sensor diagnostic.

BACKGROUND OF THE INVENTION

It is known that incomplete combustion of certain heavy hydrocarbon compounds, such as heavy oils, diesel fuel and the like may lead to particulate formation (e.g., soot). In the operation of internal combustion engines, "smoking" of the engine leads to ambient air pollution although the carbon monoxide and hydrocarbon emission of the exhaust gases itself are relatively low. It is further known to provide a particulate sensor system for detecting the level of particulate concentration emitted from an exhaust gas, as seen by reference to U.S. Pat. No. 6,634,210 entitled PARTICULATE SENSOR SYSTEM issued to Bosch et al, assigned to the common assignee of the present invention and hereby incorporated by reference in its entirety.

Bosch et al. disclose a particulate sensor system having a pair of spaced apart sensing electrodes disposed on a substrate. The sensing electrodes are coupled to a measurement circuit by way of electrically conductive leads. The operating principle of the particulate sensor is based on the conductivity of the particulates (e.g., soot) deposited on (or over) the sensing electrodes. The electrical resistance between the sensing electrodes is relatively high when the sensor is clean but such resistance decreases as soot particulates accumulate. Bosch et al. further disclose a heater that is selectively activated to burn off the soot particulates to "reset" the sensor to a known, base "clean" state. However, for diagnostic purposes, there is some difficulty distinguishing two states: (i) a faulty state such as when there is an electrical open circuit in the wiring leads, which presents as a very high resistance between the sensing electrodes, and (ii) a normal state, such as when a sensor has just been cleaned, which also presents as a very high resistance. In the former case, there is a wiring fault while in the latter case no faults exist.

In some applications, soot accumulation is very slow or only occurs when there is a malfunction in an exhaust aftertreatment device, such as a diesel particulate filter. However, the integrity of the wiring leads to the sensor must still be assured even in the absence of soot.

There is therefore a need for a particulate sensor system that minimizes or eliminates one or more of the problems noted above.

SUMMARY OF THE INVENTION

The invention is directed to a system and method for performing particulate (e.g., soot) sensor diagnostics. The present invention solves a problem in the art by providing a means to distinguish between a particulate sensor in a "clean" state, as described in the Background, and a particulate sensor that truly has a fault in the wiring (e.g., an electrical open circuit in the leads connecting the sensing electrodes to the processing circuitry).

A particulate sensor system having a diagnostic feature includes a particulate sensor and processing circuitry. The particulate sensor has a substrate, first and second sensing electrodes disposed on the substrate arranged with respect to each other to detect deposited particulates, and a heater electrode configured such that when energized according to predefined criteria, the substrate is heated to remove any deposited particulates (e.g., burn off deposited soot between or above the sensing electrodes). The heater electrode is electrically isolated from the first and second sensing electrodes.

The processing circuitry includes a heater driver, a particulate measurement circuit and a detector. The heater driver is configured to selectively energize the heater electrode in accordance with the predefined criteria mentioned above. The heater driver is further configured to produce a stimulus signal that is applied to the heating electrode. The stimulus signal will be used to verify the integrity of the connections. The particulate measurement circuit performs its conventional function and is coupled to the first and second sensing electrodes by way of first and second connecting leads. The detector is configured to determine whether the stimulus signal is present on the first and second leads when expected and generate a diagnostic signal. In operation, the sensor has a parasitic capacitance between the heater electrode and the sensing electrodes. The stimulus signal is therefore coupled through the parasitic capacitance from the heater electrode to the sensing electrodes. If the detector detects the stimulus signal, then the detector can verify the integrity of the leads since the stimulus signal was able to propagate from the sensing electrodes over the leads to the detector. However, when the detector cannot sense the stimulus signal, then the detector is configured to generate a diagnostic signal indicative of a wiring fault.

In a preferred embodiment, the heater driver is configured to generate a synchronizing signal substantially synchronous with the stimulus signal. The detector is then configured to be responsive to the synchronizing signal for detecting the stimulus signal on the leads synchronous with its generation on the heater electrode. The stimulus signal may comprise one of a pulse signal, a plurality of pulse signals defining a pulse train signal or a sinusoid signal, so long as the particular form, frequency, amplitude, and like parameters do not cause any significant heating of the substrate.

A method of performing the diagnostic is also presented.

BRIEF DESCRIPTION OF THE DRAWINGS

The present invention will now be described by way of example, with reference to the accompanying drawings.

DETAILED DESCRIPTION OF THE PREFERRED EMBODIMENT

Figure 1:
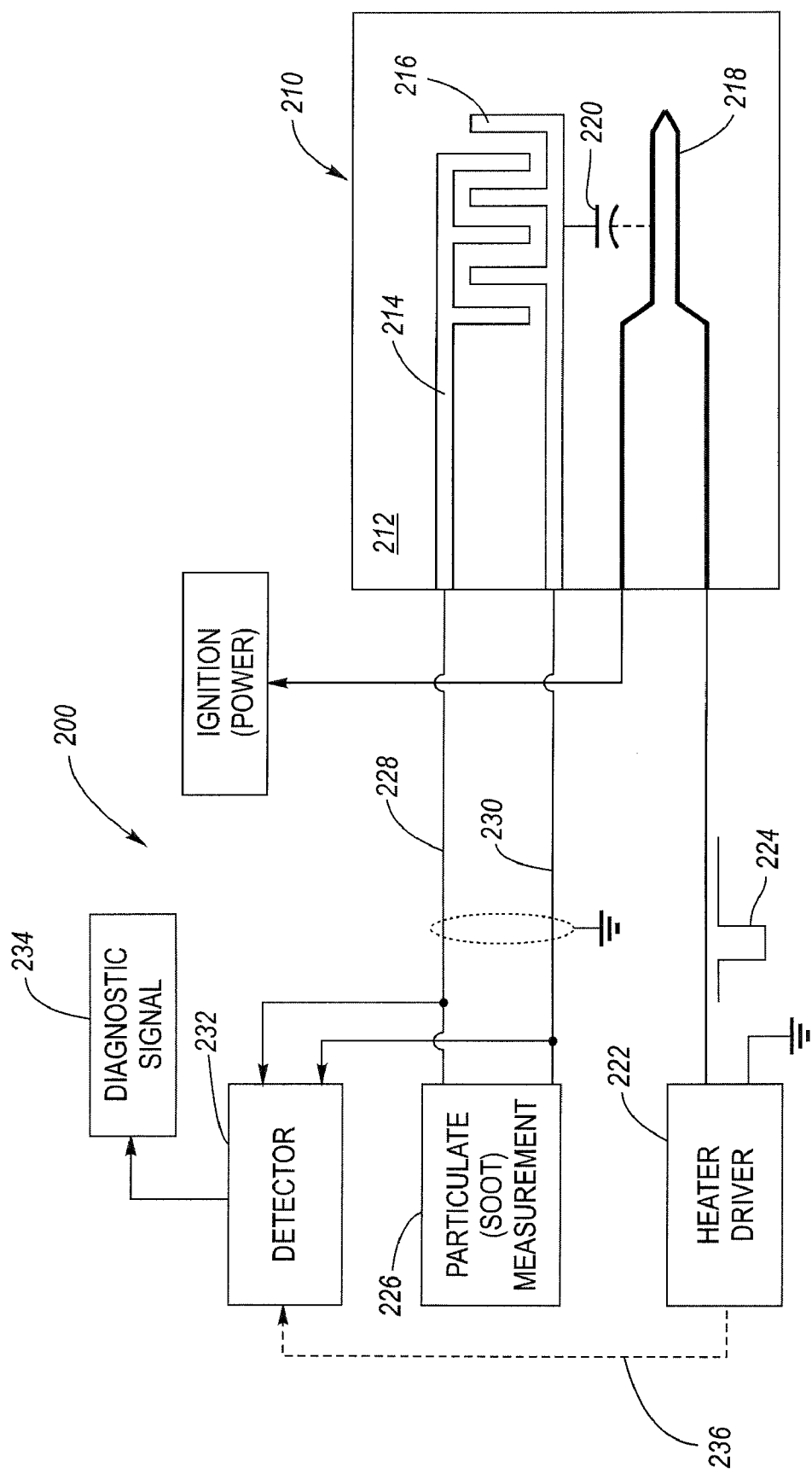
FIG. 1 is a schematic and block diagram of a particulate sensor system having a diagnostic feature for verifying the integrity of the wiring connections (i.e., leads).

Referring now to the drawings wherein like reference numerals are used to identify identical components in the various views, FIG. 1 is a schematic and block diagram of a particulate sensor system 200 having a diagnostic feature for verifying the integrity of the wiring connections between the processing circuitry and the sensor. Sensor system 200 includes a particulate sensor 210 having (i) a substrate 212, (ii) first and second sensing electrodes 214, 216 and (iii) a heating electrode 218. Due to the construction of sensor 210, there exists a parasitic capacitance 220 between the heater electrode and the sensing electrodes. System 200 further includes processing circuitry comprising a heater driver 222 configured, among other things, to generate a stimulus signal 224, a particulate (soot) measurement circuit 226, and a detector 232 configured to generate a diagnostic signal 234.

The sensor 210 is the structure that is configured to sense a particulate concentration level emitted from an exhaust gas in which it is disposed. In general, sensor 210 may be constructed with conductive inks printed on a non-conducting substrate designed to withstand exhaust gas temperatures. In this regard, sensor 210 may comprise conventional structures known in the art, for example, such as described in U.S. Pat. No. 6,634,210 entitled PARTICULATE SENSOR SYSTEM. While a more detailed description of one example of sensor 210 that may be used in the present invention will be described below in connection with FIG. 3, for purposes of the present invention, the most immediately applicable aspects of sensor 210 will be described first.

Sensing electrodes 214, 216 of sensor 210 may be disposed on substrate 212 such that a constant distance of separation between each sensing electrode is created. The width of the distance separating the sensing electrodes can vary widely, depending upon desired design parameters. The distance between the sensing electrodes will allow for a suitable amount of particulate to form between the sensing electrodes.

Heater electrode 218 is configured to heat substrate 212 when energized in accordance with predefined criteria for heating by heater driver 222 such that any deposited and accumulated particulates (e.g., soot) between or overlaying sensing electrodes 214, 216 are burned off. Heater electrode 218 is electrically isolated from sensing electrodes 214, 216, although due to the particular construction, as described above, a parasitic capacitance 220 exists between heater electrode 218 and sensing electrodes 214, 216.

Heater driver 222 is configured generally to selectively energize the heater electrode 218 in accordance with the predefined criteria described above. In one embodiment, heater driver 222 may contain switching circuitry suitable for connecting the low side of heating electrode 218 to ground to form a complete circuit (i.e., the high side of the heater electrode, as shown, is connected to a power source, such as an ignition power source, which, as known, becomes active when an operator of a motor vehicle keys on the "ignition."). When energized, electrical current flows from the power source through heater electrode 218 to ground and dissipates power in the form of heat.

In accordance with the present invention, heater driver 222 is further configured to produce an electrical stimulus signal 224 on heating electrode 218. Stimulus signal 224 that is applied to heater electrode 218 will couple to each of sensing electrodes 214, 216 via parasitic capacitance 220. There are a wide variety of forms the stimulus signal 224 can take.

Figure 2A:
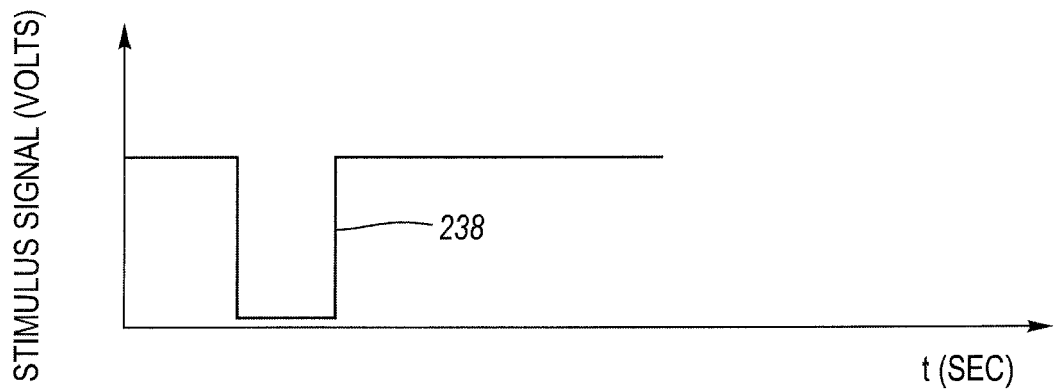
FIGS. 2A-2C are timing diagrams showing various stimulus signals for use according to the present invention.
Figure 2B:
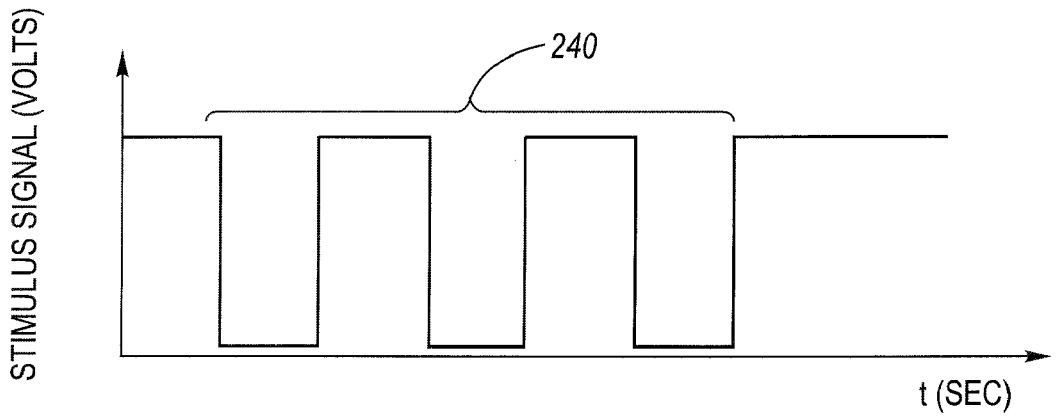
Figure 2C:
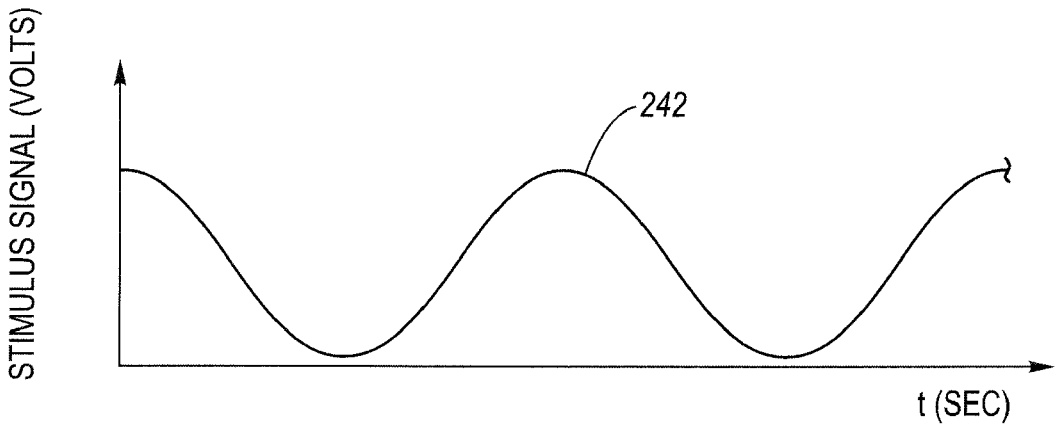

FIGS. 2A-2C are timing diagrams showing that stimulus signal 224 may take the form of a pulse signal 238, a plurality of pulse signals defining a pulse train 240 or a sinusoidal signal 242. One limit, however, on the range of signals employed as stimulus signal 224 is that it should not cause any significant heating of the substrate by virtue of it energizing heater electrode 218. It should be understood by one of ordinary skill in the art that other waveforms, suitable for verifying electrical continuity of the connector leads in the fashion described herein but not heating the substrate in any material amount, may be used.

With continued reference to FIG. 1, particulate (soot) measurement circuit 226 is coupled to sensing electrodes 214, 216 by way of first and second connector leads 228, 230. Measurement circuit 226 may be configured to perform its conventional function and thus generate an output signal (not shown) indicative of a particulate (soot) concentration level. Measurement circuit 226 may comprise conventional circuitry known in the art for performing this function, including structures based on DC voltage excitation strategies and AC voltage excitation strategies, as described more fully below in exemplary fashion.

Detector 232 is configured to detect stimulus signal 224 on leads 228, 230 and generate a diagnostic signal 234 indicative of whether or not the electrical integrity over leads 228, 230 to electrodes 214, 216 is verified. Detector 232 is configured such that when the leads to sensing electrodes 214, 216 is intact, detector 232 will be able to detect stimulus signal 224 present on leads 228, 230. However, if one or both of leads 228, 230 are faulty in some regard (i.e., short circuit, open circuit, etc.), then stimulus signal 224 will not be detected by detector 232. Detector 232 is configured then to generate a diagnostic signal 234 that indicates whether leads 228, 230 are faulty or not. Detector 232 may comprise conventional circuitry configured to perform the detection functions described above. It should be understood that the construction details of detector 232 will be dependent upon the selected stimulus signal 224.

In an alternate embodiment, additional features are provided to minimize the impact of noise that could interfere with the stimulus and detection scheme described above. First, detector 232 may alternately be configured to perform its detection function synchronously with the generation of the stimulus signal in order to better reject noise. Heater driver 222 may be further configured to generate a synchronizing signal 236, which is coupled to detector 232. In one embodiment, synchronizing signal 236 may correspond to stimulus signal 224 (i.e., in synchronism with and corresponding in shape, amplitude, etc., to stimulus signal 224). It should be understood, however, that other variations are possible, in light of the purpose of synchronizing signal 236 is to communicate the relative timing information associated with the generation of stimulus signal 224 to detector 232 to allow for synchronized capture and detection functioning of detector 232. Second, there may be a parasitic capacitance between the wire connections (i.e., leads 228, 230) to heater electrode 218 (which carries stimulus signal 224) and leads 228, 230 used for connecting measurement circuit 226 to sensing electrodes 214, 216. In this alternate embodiment, leads 228, 230 may comprise shielded wiring, which is shown in the drawings as wires having a sheath or the like coupled to ground. Shielding leads 228, 230 is operative to reduce undesirable coupling.

The present invention overcomes a problem in the art by providing the capability of verifying the integrity of the wiring connections to a particulate sensor.

While the present invention may be used to provide diagnostic capability in a wide variety of particulate sensors 210 of the type that have both sensing electrodes and a heater electrode, one exemplary particulate (soot) sensor, shown in FIG. 3 (sensor 100), will now be described so as to ensure that one of ordinary skill in the art may easily practice the invention. This exemplary sensor construction is as set forth in U.S. Pat. No. 6,634,210 entitled PARTICULATE SENSOR SYSTEM issued to Bosch et al., owned by the common assignee of the present invention and hereby incorporated by reference herein in its entirety, certain excerpts being found below. It bears emphasizing that the following detailed description of a sensor structure is not intended to be limiting as to the range and variety of structures that can be used in connection with the present invention.

Figure 3:
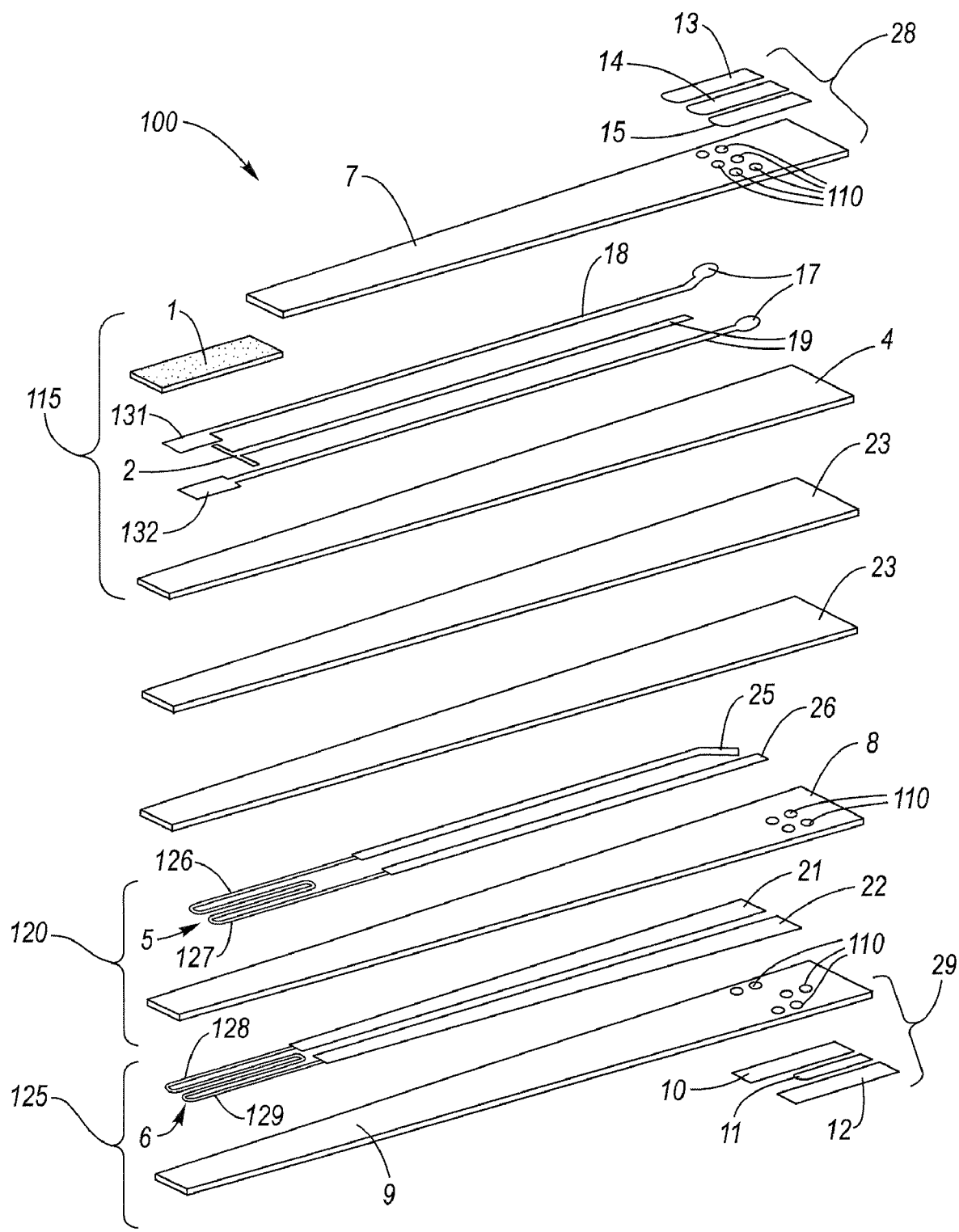
FIG. 3 is an exploded view of one exemplary particulate sensor suitable for use in connection with the present invention.

FIG. 3 is an exploded view of a typical sensor 100. The sensor is a multi-layered device having a plurality of electrically insulating layers or substrates, e.g., 4, 7, 23, 8, and 9 interspersed between the operative electrically conductive elements of the sensor. The sensor includes an electrode substrate 4 with a first sensing electrode 131 and a second sensing electrode 132 wherein each is capable of being mounted on or fixed to the same side of the electrode substrate 4. An optional guard electrode 2 may be included. This guard electrode is capable of being mounted or fixed between the sensing electrodes and electrically connected to a ground (not shown). An electrode protective layer 1 is mounted or fixed over the sensing electrodes 131 and 132 and the guard electrode 2. This entire construction forms an electrode sensor element 115. A temperature sensor 5 is mounted on an insulating temperature substrate 8 to form a temperature sensor element 120, and a heater 6 is mounted on a heater substrate 9 to form a heater element 125. A plurality of insulating substrates 23 is mounted between the temperature sensor element 120 and the electrode sensor element 115 to electrically isolate the first sensing electrode 131 and the second sensing electrode 132 from the temperature sensor 5 and the heater 6. The first sensing electrode 131 is electrically communicated with one end of a first measuring lead 18, which extends from the first sensing electrode 131 and is electrically communicated to via holes 110 formed on the isolation layer 7. The second sensing electrode 132 is electrically communicated with one end of a second measuring lead 19, which extends from the second sensing electrode 132 and is electrically communicated to via holes 110 formed on the isolation layer 7. Guard electrode 2 is disposed across the electrode substrate 4 wherein one end of the guard electrode 2 is electrically communicated with via holes 110 formed on the isolation layer 7.

Electrode protective layer 1 and electrode substrate 4 are non-movably associated with the first sensing electrode 131, the second sensing electrode 132, and guard electrode 2 to secure the first sensing electrode 131, the second sensing electrode 132, and the guard electrode 2 to the sensor 100. A dense reduction protection over-layer on top of electrodes 131 and 132 (not shown in FIG. 3) can be introduced when an AC measurement method is used. Such security is preferred as particulates condense on the sensor to create a strong reduction effect of the particulate matter, which can otherwise damage the sensing electrodes. Electrode substrate 4 is also non-movably associated with guard electrode 2 so as to secure guard electrode 2 in the sensor 100.

Temperature sensor 5 comprises a first temperature sensor end 126 and a second temperature sensor end 127. One end of a first temperature sensing lead 25 is electrically communicated with the first temperature sensor end 126 and extends to and is connected with via holes 110 formed on the insulating temperature substrate 8. One end of a second temperature sensing lead 26 is electrically communicated with the second temperature sensor end 127 and extends to and is communicated with via holes 110 formed on the insulating temperature substrate 8. Preferably, the insulating temperature substrate 8 is non-movably associated with the temperature sensor 5 and the heater 6 so as to electrically isolate the temperature sensor 5 from the heater 6.

Heater 6 includes a first heater end 128 and a second heater end 129. One end of a first heater element lead 21 is electrically communicated with the first heater end 128 and extends to and is connected with via holes 110 formed on the insulating temperature substrate 8 and the heater substrate 9. One end of a second heater element lead 22 is electrically communicated with the second heater end 129 and extends to and is communicated with via holes 110 formed on the insulating temperature substrate 8 and the heater substrate 9. In addition, sensor 100 preferably includes a heater substrate 9 non-movably associated with heater 6 so as to electrically isolate heater 6 from a second contact pad 29.

The first measuring lead 18, second measuring lead 19, and the guard electrode 2 are electrically communicated with a first contact pad 28, wherein the first contact pad 28 comprises a first ground terminal 13, a first resistance measurement terminal 14, and a second power terminal 15. The first measuring lead 18 is preferably electrically communicated with the first ground terminal 13, the second measuring lead 19 is preferably electrically communicated with the second power terminal 15, and the guard electrode 2 is electrically communicated with the first resistance measurement terminal 14.

The first heater element lead 21 is preferably electrically communicated with the first temperature sensing lead 25 such that the temperature sensor can serve as an alkaline impurity getter. By removing the alkaline impurities condensed on the heater, the temperature sensor serves to prolong the usability of both the heater and the sensing electrodes. While not damaging the temperature sensor since the accumulated alkaline impurity does not change the temperature sensor's total resistive characteristics to any significant degree. The electrical communication between heater 6 and temperature sensor 5 comprises connecting a first temperature sensing lead 25 with the first heater element lead 21, such that the lead from the temperature sensor is electrically connected to the negative polarity lead of the heater. The electrical connection may be made by way of via holes 110 formed on the insulating temperature substrate 8.

The second temperature sensing lead 26 and second heater element lead 22 are electrically connected to a second contact pad 29. The second contact pad 29 comprises a second ground terminal 10, a second resistance measurement terminal 11, and a first power terminal 12.

The second heater element lead 22 can be electrically communicated with the first power terminal 12; the second temperature sensing lead 26 can be electrically communicated with the second resistance measurement terminal 11; and the first temperature sensing lead 25 can be electrically communicated with the first heater element lead 21, wherein the first heater element lead 21 can also be electrically communicated with the second ground terminal 10.

The particulate sensor system comprises a sensor in electrical communication with a sensor circuit, which operates to detect the level of particulate matter in the environment surrounding the sensor. The particulate sensor system may be calibrated to detect a specific amount of particulate accumulation on the sensor, at which point the particulate sensor system removes the particulates (self-regeneration) by signaling a heater disposed in the sensor. Additionally, the particulate sensor system may be designed such that after a predetermined number of self-regeneration cycles, particles condensed on an exhaust system can also be removed. It is noted that each self-regeneration cycle can be determined based on the size dimensions of the sensor; in general, the smaller the sensing area (e.g., the substrate surface upon which the sensing electrodes are positioned) and the smaller the volume at the tip of the sensor (e.g., that portion of the sensor where the sensing electrodes are positioned), the less time is needed for each self-regeneration cycle. Additionally, a temperature sensor may be advantageously used to maintain the external temperature surrounding the sensor at a point higher than the condensation point of water but lower than the condensation point of the particulates such that the particulates can condense on the sensor without an accompanying condensation of water. Preferably the external temperature maintained by the heater is above the temperature of water condensation, and below the burn-off temperature of the deposited particulates.

The particulate sensor system can self-regenerate by a signal comprising an electrical communication between at least two sensing electrodes and a heater. A signal is transmitted from the sensing electrodes to the heater when the electrical resistance between the sensing electrodes drops to a predetermined threshold amount. Such a drop in resistance is caused by particulate condensation on the sensor. The signal activates the heater to increase its thermal energy output, thereby causing the removal of the particulates from the sensor. As the particulates are removed from the sensor, the resistance gradually increases. The increasing resistance can be employed to signal the heater to decrease its thermal energy output, or the thermal energy output can be maintained until the resistance reaches a selected level, or thermal energy output may be controlled at timed intervals.

The sensing electrodes can include metals, such as, gold, platinum, osmium, rhodium, iridium, ruthenium, aluminum, titanium, zirconium, and the like, as well as, oxides, cermets, alloys, and combinations comprising at least one of the foregoing metals. In an exemplary embodiment, the sensing electrode can comprise a platinum/alumina cermet wherein the platinum is about 90 wt % (weight percent) to about 98 wt % of the sensing electrode, with about 93 wt % to about 95 wt % platinum particularly preferred, where weight percent is based on the total dry weight of the cermet. Each sensing electrode may be composed of the same or different material as the other sensing electrode(s).

The sensing electrodes can be formulated in any fashion. Preferably, however, the sensing electrodes are formed by first preparing an ink paste by mixing an electrode forming-metal powder (e.g., platinum, gold, osmium, rhodium, iridium, ruthenium, aluminum, titanium, zirconium, and the like, or combinations of at least one of the foregoing) with oxides in a sufficient amount of solvent to attain a viscosity suitable for printing. The oxides used to form the sensing electrodes may include those oxides that do not promote the oxidation of particulates and that do not lower the burn-off temperature of the particulates. Non-suitable oxides are, e.g., copper oxide, cerium oxide, and iron oxide. The ink paste forming the sensing electrode can then be applied to an electrode substrate via sputtering, chemical vapor deposition, screen printing, flame spraying, lamination, stenciling, or the like, with screen printing particularly preferred.

The sensing electrodes are preferably disposed onto the electrode substrate such that a constant distance of separation between each sensing electrode is created. The width of the distance separating the sensing electrodes can vary widely, depending upon desired design parameters. A preferred distance comprises a width of separation of about 0.1 to about 0.5 millimeter (mm), with about 0.1 to about 0.3 mm particularly preferred, and about 0.1 mm especially preferred. The distance between the sensing electrodes will allow for a suitable amount of particulate to form between the sensing electrodes, and will also allow for the positioning of a guard electrode between the sensing electrodes where appropriate.

The size and geometry of the sensing electrode is preferably selected to allow for current output sufficient to enable reasonable signal resolution over a wide range of particulate concentrations. Generally, a thickness of about 5 to about 25 micrometers can be employed, with a thickness of about 8 to about 20 micrometers preferred, and about 10 to about 18 micrometers particularly preferred. The sensing electrode can be of any shape, for example, rounded, squared, polygonal, such as square, needle-shaped, round, oblong, inter-digital, or the like.

The optional guard electrode is most preferably included in the sensor when an alternating current (AC) method is used to detect conductivity (complex impedance). The AC method is ideally employed where a sensor more sensitive than that obtained using a DC method is desired. The differing sensitivity created by AC or DC methods is a result of the way in which the particulates are detected. For example, sensing, and hence, quantification, of particulate accumulation by the DC method, requires that the particulates be in direct physical contact (bridging) with other deposited particulates. Therefore, particulate sensing is limited to those deposited particulates in direct contact with other deposited particulates. Such direct contact occurs only when a sufficient amount of particulates deposit on the surface between the two electrodes. When particulate deposition is insufficient, and there is not enough direct particle contacts to form a direct conducting bridge between the electrodes, there is no DC current flow, and the sensor cannot detect the presence of deposited particulates. The AC method, however, can detect a greater range of particulates as AC can conduct current among the non-contacting particulates through capacitance effect, and hence, can sense non-bridged particulates. In this way, a full range (e.g., up to about 100%) of particulate concentrations can be measured using an AC method as compared to a range of about 15-25% detected when using a DC method (numbers are based on the commonly known percolation theory). In general, the higher the AC frequency, the more sensitive the sensor.

The AC guard electrode is preferably disposed along the length of the electrode substrate, and is preferably positioned between the sensing electrodes up to the area wherein the deposited particulates can be detected. The guard electrode can eliminate any stray capacitance between the sensing electrodes from the background measurement data and thereby improve the signal to noise ratio. The use of AC detection can also protect the two measurement electrodes from direct exposure to the exhaust gas. Under the AC method, the sensing electrodes can be covered with an over-layer, preferably a thin over-layer, (e.g., a thickness of up to about 60 micrometers), of a dense glass (glazing materials), oxides (e.g., alumina), or combinations comprising at least one of the foregoing. The over-layer can protect the sensing electrodes against reduction of the particulates when they are burned off. Typically, when the particulates are burned off, oxygen is consumed, thereby creating a reducing atmosphere locally. This reducing atmosphere, in turn, can reduce the weak oxide bonding between the sensing electrodes and the substrate, and can de-bond the sensing electrodes from the substrate. An over-layer, however, can protect the sensing electrodes, and the AC frequency current can still flow through the over-layer to engage the deposited particulates. The over-layer can be done with doctor-bladed cast tape, or with commercial glazing products. Preferably, the over-layer comprises a dense glass or oxide to hinder the reducing atmosphere from penetrating underneath the sensing electrodes where the sensing electrodes contact the substrate.

Both the heater and the temperature sensor, forming in whole or in part, the heating element, can comprise various materials. Possible materials include platinum, gold, palladium, and the like; and alloys, oxides, and combinations comprising at least one of the foregoing materials, with platinum/alumina, platinum/palladium, platinum, and palladium preferred. The heater and temperature sensor can be applied to the sensor in any fashion, such as by sputtering, chemical vapor deposition, screen printing, flame spraying, lamination, and stenciling among others where screen printing is particularly preferred. Furthermore, the heater can comprise a thickness of about 3 to about 50 micrometers, with about 5 to about 30 micrometers preferred, and about 10 to about 20 micrometers more preferred.

The sensor may further comprise various substrates useful in electrically isolating and protecting the sensing element and the heating element from the temperature surrounding the sensor and/or from the thermal reduction of the condensed particulates during the self-regeneration cycles. The substrates include, but are not limited to, an electrode protective layer, an electrode substrate, an isolation layer, an insulating temperature substrate, a heater substrate, insulating substrates, wherein the number of insulating substrates is sufficient to prevent disruptive ionic or electrical communication between the heating element and the sensing electrode (e.g., preferably about 2 to about 3 insulating substrates), and combinations comprising at least one of the foregoing.

The substrates can comprise non-ionically conducting, electrically insulating materials. Possible electrically insulating materials include oxides, such as alumina, zirconia, yttria, lanthanum oxide, silica, and combinations comprising at least one of the foregoing, or any like material capable of inhibiting electrical communication and providing physical protection, wherein alumina is particularly preferred. In order to hinder electrical communication between the components of the sensor, the substrates are preferably composed of a high purity oxide; e.g., less than about 10.0 wt % impurities, with less than about 8.0 wt % preferred, and less than about 5.0 wt % more preferred, wherein the weight percent of the impurities is based on the total weight of the substrate. Although the composition of the individual substrates can vary, preferably they comprise a material having substantially similar coefficients of thermal expansion, shrinkage characteristics, and chemical compatibility in order to minimize, if not eliminate, delamination and other processing problems. Alkaline (e.g., sodium, potassium, lithium, and the like) oxides should be avoided as they can be easily reduced to form impurities in the heater, temperature sensor, and the sensing electrodes.

In general, each of the substrates can be of sufficient size to support the entire length of the sensing electrodes, the temperature sensor, and/or the heater. The thickness of each substrate can be determined based on the desired thermal response time of the self-regeneration cycle, where shorter thermal response times require a smaller thickness. Preferably, the thickness of each substrate can be up to about 200 micrometers thick, with a thickness of about 50 to about 180 micrometers more preferred, and about 140 to about 160 micrometers especially preferred. The substrates can be formed using ceramic tape casting methods, and the like.

Any number of the substrates can be porous, dense, or both porous and dense. The porosity or the diameter of the pores can be controlled to limit the various sizes of particulates that can reach the sensing electrodes, and to limit the size of particulates that can penetrate and trap within the porous layer. In general, larger-sized particulates (e.g., particles having a diameter along the major axis equal to or greater than about 5 micrometers) interfere with current conduction more than do smaller-sized particulates (e.g., particles having a diameter along the major axis less than about 5 micrometers). Therefore, where more precise conductance measurements are desired, it is especially desirable to exclude the larger particulates from accumulating onto or between the sensing electrodes. Such exclusion can be achieved by controlling the size and/or the number of pores on the substrate, and/or by controlling the internal tortuousness of the substrate. Here, tortuousness is defined as the effective path length through the connected pores per standard thickness of the layer.

Pore size can be controlled by the size of the fugitive materials used, e.g., by controlling the size of carbon black or graphite, where fugitive materials are those materials that burn off at high temperatures leaving behind pores with controlled sizes. Tortuousness depends on the texture of the substrate-forming oxide powder used to form the substrate. Texture, in turn, can be controlled by firing the substrate-forming oxide powder at a high temperature to coarsen the substrate-forming powder, and then sieving the substrate-forming metal powder to the right size range for slurry making.

Preferably, where the substrate comprises the electrode protective layer, there is a space gap (e.g., about 10 to about 50 micrometers) between the electrode protective layer and the sensing electrodes to allow for the free deposition of particulates after penetrating the porous electrode protective layer. Applying a fugitive layer between the sensing electrode area and the porous layer, which can be burned off during the firing stage, can create the space gap. Screen printing can be used to deposit such layers.

After acquiring the components of the sensor, the sensor is preferably constructed according to thick film multilayer technology such that the thickness of the sensor allows for good thermal response time toward the thermal cycle of sensor regeneration. A preferable thickness is about 0.1 to about 3.0 millimeter (mm), with about 0.15 to about 2.5 mm particularly preferred, and about 0.3 to about 1.22 mm especially preferred. To increase the thermal mechanical strength (thermal shock) of the sensor, the tip of the sensor is preferably as small as possible, yet large enough for ease of manufacturing. Therefore, the tip of the device can comprise a length of about 0.5 to about 4.5 mm, with about 1.0 to about 4.0 mm preferred, and about 1.0 to about 2.0 mm more preferred. To accommodate the top and bottom contact pads at the end portion of the device where thermal shock is of no concern, the width of the sensor can be about 4 to about 8.5 mm, with about 4.5 to about 8.0 mm preferred, and about 5.0 to about 6.0 mm more preferred.

It is to be understood that the above description is merely exemplary rather than limiting in nature, the invention being limited only by the appended claims. Various modifications and changes may be made thereto by one of ordinary skill in the art, which embody the principles of the invention and fall within the spirit and scope thereof.

The invention claimed is:

1. A particulate sensor system, comprising:
a particulate sensor having (i) a substrate; (ii) first and second sensing electrodes disposed on said substrate and arranged with respect to each other to detect deposited particulates; and (iii) a heater electrode configured to heat said substrate so as to remove any deposited particulates, said heater electrode being electrically isolated from first and second sensing electrodes;
a heater driver configured to selectively energize said heater electrode, said heater driver being further configured to produce a stimulus signal on said heating electrode;
a particulate measurement circuit coupled to said first and second sensing electrodes by way of respective first and second leads; and
a detector configured to detect said stimulus signal on said first and second leads and generate a diagnostic signal indicative of verified electrical conductivity over said leads to said sensing electrodes.

2. The sensor system of claim 1 wherein said heater driver is further configured to generate a synchronizing signal substantially synchronous with said stimulus signal, said detector being responsive to said synchronizing signal for detecting said stimulus signal.

3. The sensor system of claim 1 wherein said stimulus signal comprises one of pulse signal, a plurality of pulse signals defining a pulse train signal, and a sinusoid signal.

4. The sensor system of claim 1 wherein said sensor has a respective capacitance between said heater electrode and said first and second sensing electrodes, said stimulus signal being coupled from said heater electrode to said first and second sensing electrodes by way of said capacitances.

5. The sensor system of claim 1 wherein said particulate comprises soot.

6. The sensor system of claim 1 wherein said leads comprise shielded wires.

7. The sensor system of claim 1 wherein said detector is configured to generate said diagnostic signal indicative of an electrical fault in said leads.

8. The sensor system of claim 7 wherein said electrical fault comprises one of a short and an open.

9. The sensor system of claim 8 wherein said detector is configured to detect said stimulus signal on said first lead independently of said second lead, said detector being further configured to detect said stimulus signal on said second lead independently of said first lead.

10. A particulate sensor system having a diagnostic capability, comprising:
a soot concentration sensor having (i) a substrate; (ii) first and second sensing electrodes disposed on said substrate and arranged with respect to each other to detect deposited soot therebetween; and (iii) a heater electrode configured to heat said substrate so as to remove any deposited soot, said heater conductor being electrically isolated from first and second electrodes;
a heater driver configured to selectively activate said heater, said heater driver being further configured to produce a stimulus signal on said heating conductor;
a soot measurement circuit coupled to said first and second electrodes by way of respective first and second leads, said soot measurement circuit being configured to generate an output signal indicative of a soot concentration level; and
a detector configured to detect said stimulus signal on said first and second leads and generate a diagnostic signal indicative of verified electrical conductivity over said leads to said electrodes.

11. A method of performing a diagnostic on a particulate sensor having a pair of sensing electrodes and a heater electrode, said method comprising the step of detecting a stimulus signal applied to the heater electrode on a lead connected to one of the sensing electrodes to verify the electrical integrity of the lead.

12. The method of claim 11 further comprising the steps of:
providing a substrate on which the sensing electrodes are disposed;
generating a synchronizing signal synchronous with the stimulus signal;
detecting the stimulus signal on the lead in accordance with the synchronizing signal.

13. The method of claim 12 further comprising the steps of:
generating a fault signal when the stimulus signal is not detected at a time when the stimulus signal is being applied to the heater electrode.

* * * * *